(12) United States Patent
Shoshan

(10) Patent No.: US 6,217,522 B1
(45) Date of Patent: Apr. 17, 2001

(54) METHOD AND SYSTEM FOR DETERMINATION OF THE PRESSURE-VOLUME RELATIONSHIP OF THE HEART

(75) Inventor: Ofer Shoshan, Safed (IL)

(73) Assignee: Pyrotec Limited, Zurich (CH)

( * ) Notice: Subject to any disclaimer, the term of this patent is extended or adjusted under 35 U.S.C. 154(b) by 0 days.

(21) Appl. No.: 09/051,401

(22) PCT Filed: Oct. 4, 1996

(86) PCT No.: PCT/IB96/01052
§ 371 Date: Dec. 3, 1998
§ 102(e) Date: Dec. 3, 1998

(87) PCT Pub. No.: WO97/12547
PCT Pub. Date: Apr. 10, 1997

(30) Foreign Application Priority Data

Oct. 6, 1995 (IL) ........................................................ 115538

(51) Int. Cl.[7] .................................................... A61B 5/02
(52) U.S. Cl. ........................ 600/490; 600/485; 600/493; 600/453; 600/454; 600/455
(58) Field of Search ...................................... 600/481, 483, 600/485, 490, 493, 496, 526, 528, 455, 453, 454

(56) References Cited

U.S. PATENT DOCUMENTS

| | | | |
|---|---|---|---|
| 5,086,776 | * 2/1992 | Fowler et al. | 600/455 |
| 5,370,122 | * 12/1994 | Kunig et al. | 600/483 |
| 5,634,467 | * 6/1997 | Nevo | 600/490 |

* cited by examiner

Primary Examiner—Cary O'Connor
Assistant Examiner—Navin Natnithithadha
(74) Attorney, Agent, or Firm—Herbert Dubno

(57) ABSTRACT

A pressure volume loop of the heart of a patient is obtained utilizing an electrocardiograph and a brachial-artery pressure cup pressure-measurement system having an echo-Doppler sensor positioned to measure the flow waves at the aortic root.

12 Claims, 3 Drawing Sheets

METHOD AND SYSTEM FOR DETERMINATION OF THE PRESSURE-VOLUME RELATIONSHIP OF THE HEART

CROSS REFERENCE TO RELATED APPLICATIONS

This application is a national stage of PCT/IB96/01052 filed Oct. 4, 1996 and based, in turn, on a national application in Israel 115538 of Oct. 6, 1995 under the International Convention.

FIELD OF THE INVENTION

The present invention relates to a method and system for the non-invasive determination of the pressure-volume loop (PVL) of the heart.

BACKGROUND OF THE INVENTION

The heart, as is known, is a pump and, as such, produces pressure that causes the blood to circulate through the system. A widely used graphic representation of the cardiac function is known as the pressure-volume loop (PVL), referring to the relationship, in the left ventricle, between pressure and volume during a single cardiac cycle which consists of four main phases: (1) the heart being filled with blood; (2) the heart generating enough pressure to overcome arterial resistance; (3) the heart ejecting blood into the arteries, and (4) pressure in the heart dropping so that it is ready to receive blood again.

PVLs have a variety of uses. They have been found to reliably depict various external influences on the heart, such as exercise, drug therapy, cardiac disease, etc. PVLs are an irreplaceable research tool in the field of cardiac mechanics, and are extensively used in the teaching of medical students. Other parameters which can be determined with the aid of the method and system according to the present invention include cardiac power, cardiac peak power and contractile reserve.

Cardiac power, the power of the heart muscle, representing the pumping capability of the heart (in units of work/time), is a known index of the heart's pumping ability to increase power has been shown to be directly related to the survival of patients with severe heart failure [Tan, 1987]. Recent studies have shown the cardiac peak power, i.e., the maximum instantaneous cardiac power during blood ejection, to be an accurate descriptor of the heart's contractility, the quality of the heart muscle, representing its ability to contract [Kass and Beyar, 1991].

The present invention measures cardiac power as well as power increase under stress, thus calculating contractile reserve (CR), the difference between cardiac peak power and cardiac power at rest. CR can be used to arrive at a prognosis for heart failure patients, and thus to decide the timing of heart transplantation or other therapy. CR is an excellent tool for following the treatment of heart patients and for diagnosing heart disease.

Despite its many uses, no easy way has so far been found to produce PVLs. The only method of doing so until now has been by means of cardiac catheterization, which is an invasive procedure that, as all invasive procedures, puts the patient at a non-negligible risk, is very costly in that it requires a large, highly trained staff, and consequently is not performed in every hospital.

OBJECT OF THE INVENTION

It is thus one of the objects of the present invention to provide a method for determining a patient's PVL by exclusively non-invasive and therefore non-hazardous means, a method that can be applied by a relatively small team of medical personnel mostly on the technician level, and that is therefore within the means of even small medical facilities.

SUMMARY OF THE INVENTION

According to the present invention, the above object is achieved by providing a method for the non-invasive determination of the pressure-volume loop (PVL) of a patient's heart, comprising the steps of connecting said patient to an electrocardiograph; mounting the probe of an echo-Doppler device on the patient in a position enabling it to sense the aortic root and to produce signals representative of the flow waves issuing from said aortic root; analyzing said signals and obtaining a series of data points as pairs of flow and time, using the QRS complex of the electrocardiogram pattern as a time reference point; applying a curve-fitting procedure to turn said data points into a flow curve resembling the flow wave issuing from said aortic root; placing a pressure cuff on the patient's arm and inflating it to a point where all flow in the patient's brachial artery stops; deflating said cuff throughout deflation; during deflation, sensing blood flow penetrating the barrier constituted by said pressurized cuff, with instantaneous pressure at the aortic root being equal to instantaneous pressure inside said cuff; obtaining a series of data points from peak systolic to diastolic pressure, each point consisting of cuff pressure at penetration coupled with the time of its occurrence after the corresponding QRS complex; applying a curve-fitting procedure to turn said data points into a pressure curve resembling the ascending limb of the aortic pressure wave; calculating the end systolic pressure (ESP) using the expression $ESP=DP+\frac{2}{3}(PSP-DP)$, where DP=diastolic pressure and PSP=peak systolic pressure; calculating volume at point ESP by integrating said flow curve throughout the ejection phase of the patient's heart, and viewing said PVL on a monitor screen.

The invention further provides a system for the non-invasive determination of the pressure-volume loop (PVL) of a patient's heart, comprising electrocardiograph means having electrodes attachable to selected points on the body of said patient; a pressurizable cuff mountable on an arm of said patient; computer means provided with display means connectable to said electrocardiograph means and to said pressurizable cuff via a pressure card, and monitoring means locatable externally of said patient in such a position as to be capable of monitoring the aortic root of said patient's heart, the output of said means leading at least indirectly to said computer means.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

The above and other objects, features, and advantages will become more readily apparent from the following description, reference being made to the accompanying drawing in which.

In the drawings.

SPECIFIC DESCRIPTION

Figure 2:
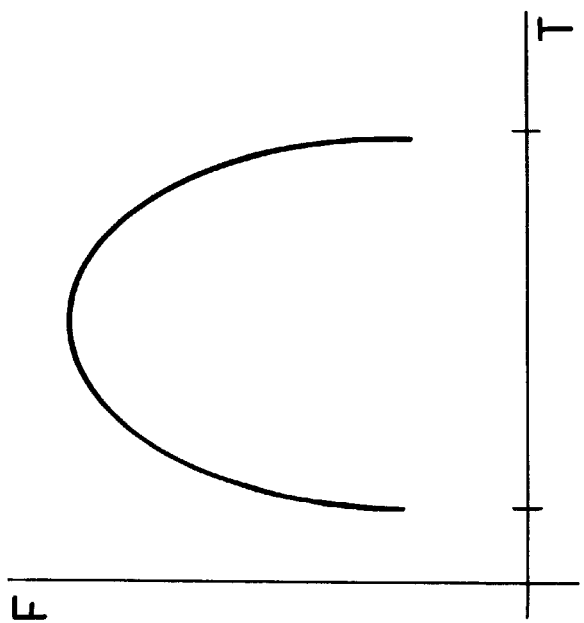
FIG. 2 shows the flow curve F (flow) vs. T (time)

The method according to the invention requires, in principle, the taking of two measurements, neither of them invasive: (1) measurement of instantaneous flow in the aortic root (FIG. 2) by means of a commercially available echo-Doppler device; and (2) measurement of instantaneous pressure in the aortic root (FIG. 3) by means of a pressure cuff, in combination with an ECG monitor of the well-known type, and the plotting of flow and pressure curves yielded by these measurements.

The invention resides in the way data from these two measurements are combined to yield the PVL, the curve representing pressure vs. volume, as well as in the derivation of cardiac power and contractile reserve from these non-invasive measurements.

Figure 1:
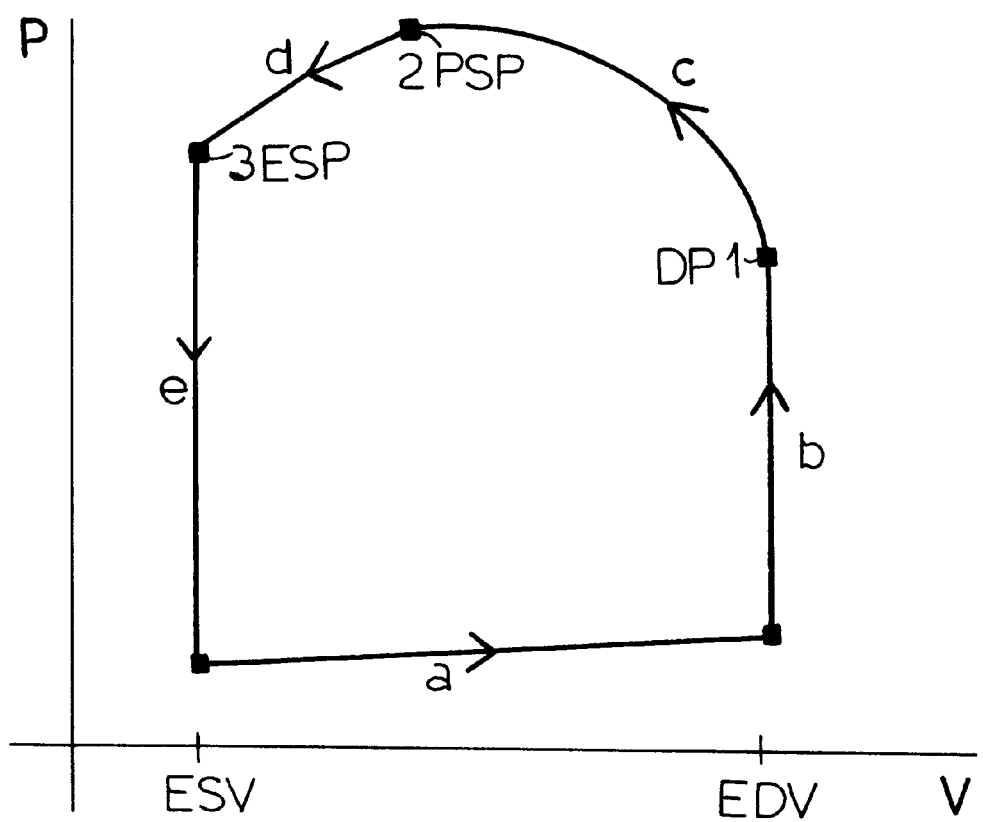
FIG. 1 represents a PVL, including the diastolic point (DP), the peak systolic point (PSP) and the end systolic point (ESP)

Referring now to the drawings, there is shown in FIG. 1 a complete PVL, seen to consist of five segments a, b, c, d and e.

Segment a, representing the filling of the heart with blood, is approximated by a linear curve with a predetermined empirical slope which is easily found in the literature.

Segment b, representing the phase in which the heart contracts, pressure rises and the aortic valve opens (at point 1) when diastolic pressure has been reached, is a straight, vertical line leading from segment a to the diastolic point DP (point 1), at an abscissa of EDV (end diastolic volume).

Figure 3:
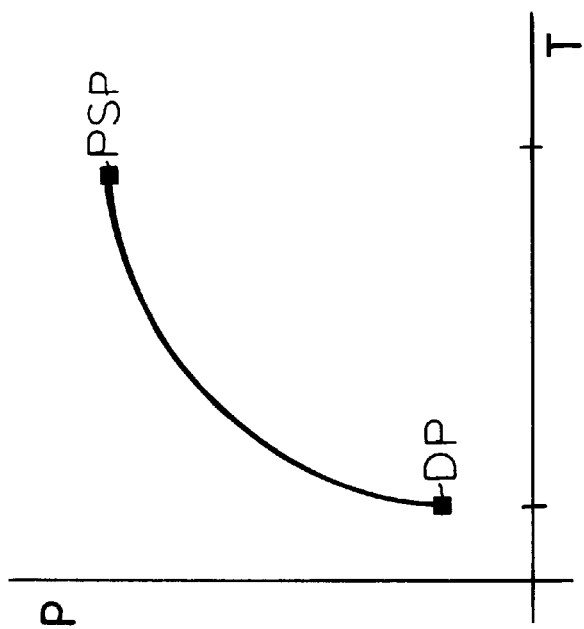
FIG. 3 is the pressure curve P (pressure) vs. T (time), including DP and PSP.

Segment c, representing that phase of the cardiac cycle in which blood is ejected into the arteries, with pressure starting from DP and reaching its peak at point 2 (peak systolic point—PSP), also represented in the P vs T curve of FIG. 3, is the clinically most important section of the PVL.

Segment d represents that part of the cycle in which pressure drops from PSP to EPS (end systolic point), i.e., from point 2 to point 3. It is approximated by a straight line.

Segment e, a vertical line starting at ESP (point 3), represents that part of the cycle in which the heart muscle fully relaxes, resulting in an immediate pressure relief. Segment e joins segment a above point ESV (end systolic volume) on the abscissa.

While segments b, d and e are easily constructed, being straight lines, and segment a can be found in the literature, segment c is a function of several parameters, the determination of which is described further below.

Cardiac power represents the product of cardiac systolic flow and cardiac systolic pressure, as shown in the following equation:

$$\text{Cardiac power} = \text{flow}_{sys} \times \text{pressure}_{sys} \tag{1}$$

where:

$\text{flow}_{sys}$ is aortic flow, computed from the velocity/time integral×aortic valve area measured in the apical four-chamber view by echo-Doppler, and $\text{pressure}_{sys}$ is central aortic pressure measured by the invention, as described above and below.

Cardiac peak power represents the maximal product of the above equation:

$$\text{Peak power} = \text{mas}(\text{flow}_{sys} \times \text{pressure}_{sys}) \tag{2}$$

As stated above, recent experimental data indicate that peak power is an index of contractility. Contractile reserve can thus be calculated by measuring cardiac power at rest and under maximal stress, and calculating the difference:

$$\text{Contractile reserve} = \text{peak power}_{max} - \text{peak power}_{rest} \tag{3}$$

As mentioned above, calculation of the PVL, cardiac power and contractile reserve, is made possible by two non-invasive measurements: the measurement of instantaneous flow at the aortic root, and the measurement of instantaneous pressure at the aortic root.

These measurements are described below in conjunction with FIG. 4.

Figure 4:
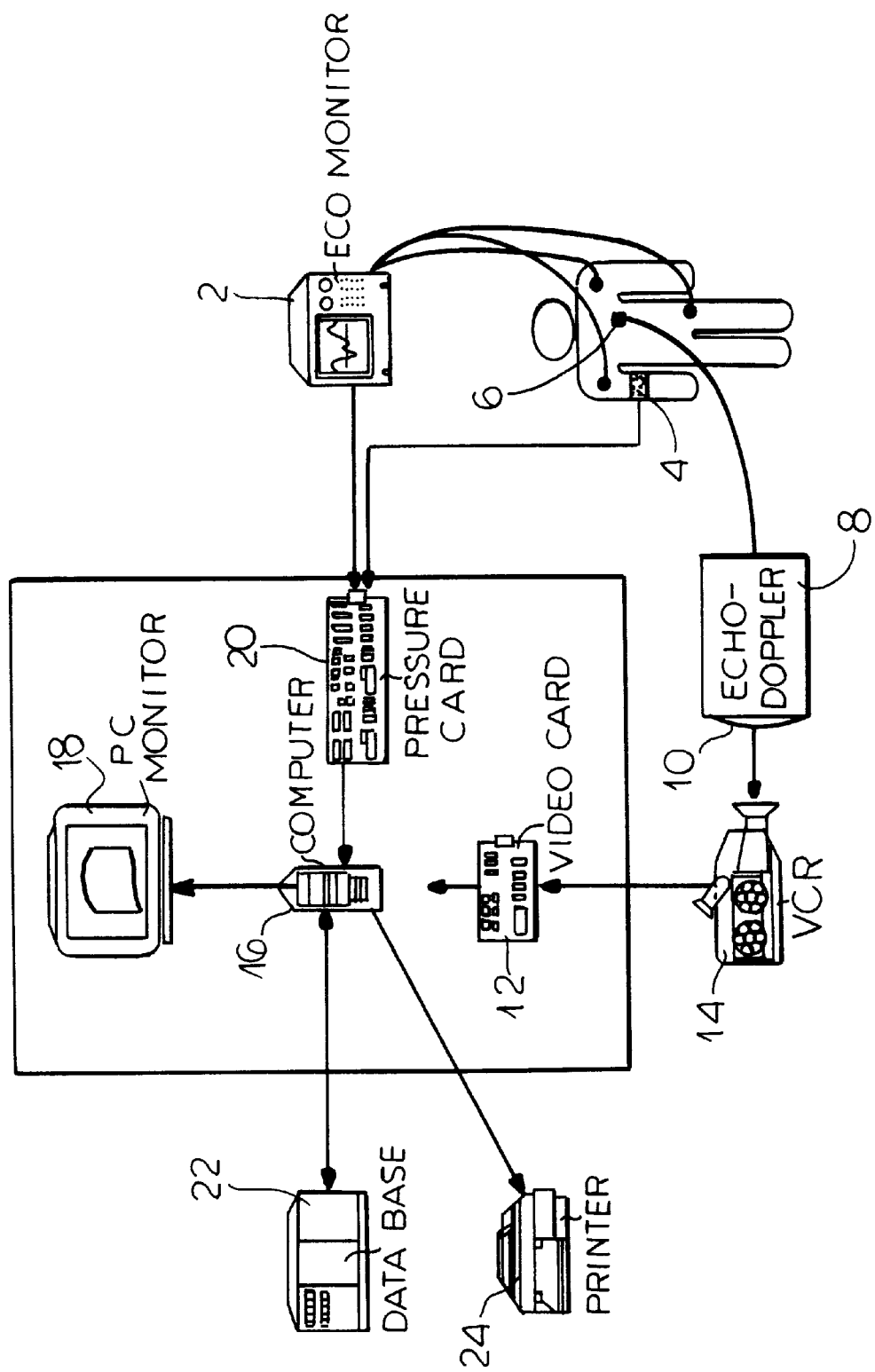
FIG. 4 is a block diagram of the system according to the invention.

In the block diagram of FIG. 4, the patient is connected to a standard electrocardiograph (ECG) 2 and wears a slightly modified pressure cuff 4 of the type used in blood-pressure measurements.

To establish the flow curve (FIG. 2), probe 6 of a per se known echo-Doppler device (EDD) 8 is placed in an apical four-chamber position so that it can "view" the aortic root. Velocity waves emerging from the aortic root are imaged on display screen 10 when the EDD is in the Doppler mode. Flow can then be calculated from the expression:

Flow = velocity × valve area.

Simultaneously with the display of the flow waves, the technician runs a commercially available video image grabbing program (VIG), installed together with the appropriate video card 12.

Using the VIG program with the EDD, the technician selects a frame that displays the velocity wave to best advantage. This frame is then recorded by VCR 14 and stored in the memory of computer 16 or other electronic means, for subsequent processing.

While in the preferred embodiment of the invention an echo-Doppler device is used to record blood flow velocity at the aortic root, the same purpose can be achieved by using a per se known gamma-camera, or any equivalent equipment which replaces the EDD 8, the VCR 14 and the video card 12.

For processing, the technician runs a flow-analysis program (FA) that guides him through the following steps:

1. The selected flow image is displayed on the screen of PC monitor 18.

2. The technician marks the region of interest within the displayed flow wave.

3. The FA program automatically detects the flow wave contour and stores it as a series of data points, consisting of pairs of flow and time.

4. The time is estimated by the FA program by detecting the QRS complex of the ECG pattern displayed as a standard feature on the EDD flow image. The time of each data point is estimated relative to the QRS complex, in milliseconds.

5. The FA program then loads the stored data points, and, using a polynomial 4th degree fit, generates a flow curve accurately resembling the original flow wave.

6. The flow curve is stored on the computer disk for further processing.

To establish the pressure curve, a device is used to non-invasively measure the pressure at the aortic root which, in the form of pressure card 20, simultaneously receives input from ECG monitor 2 and pressure cuff 4.

The procedure is as follows:

1. Cuff 4 is placed on the patient's arm above the brachial artery and inflated to a pressure exceeding the peak systolic pressure of the patient. At that pressure, flow in the brachial artery completely stops.

2. Cuff 4 is allowed to deflate at a controlled rate, with pressure inside cuff 4 being measured on-line throughout deflation.

3. Card 20 is connected to the sync output of monitor 2, and recordings are made of the internal clock time of computer 16, as well as of the QRS complexes detected by monitor 2.

4. A sensor (possibly based on sound, flow, pressure, magnetic detection, etc.), placed inside, proximal or distal to cuff 4, is used to detect, during deflation, blood flow penetrating the barrier constituted by the pressure cuff. Such penetration occurs the moment brachial pressure equals or slightly exceeds cuff pressure. It is a proven scientific fact that, at this point, pressure in the brachial artery equals the pressure in the aortic root, hence it equals the pressure in cuff 4.

5. As the QRS complex, cuff penetration point and internal clock time are sampled simultaneously and on-line, time between the QRS complex and cuff penetrtion can be measured and stored.

6. As the pressure in cuff 4 decreases, the time to cuff penetration decreases until the patient's diastolic pressure is reached, where the time becomes constant. A series of data points is generated from peak systolic to diastolic pressure, each consisting of cuff pressure at penetration coupled with the time of their occurrence after the corresponding QRS complex. The data points are stored for further processing.

7. For processing the recorded data, a pressure analysis program (PA) is run, which loads the stored data points and, using a polynominal 4th degree fit, generates a presure curve accurately resembling the ascending limb of the aortic pressure wave.

8. The pressure curve (FIG. 3) and the flow curve (FIG. 2) are analyzed at the corresponding instantaneous time point.

9. The pressure value (P) is taken from the pressure curve.

10. The volume value (V) is calculated by integrating instantaneous flow up to that time point.

11. Points P and V are presented in the diagram in order to draw segment c up to PSP (point 2, FIG. 1).

12. The curve between PSP and ESP (point 3, FIG. 1) is approximated by a straight line.

13. Pressure at point ESP is calculated, using the expression:

ESP=DP+⅔ (PSP−DP).

14. Volume at point ESP is calculated by integrating the flow curve throughout the ejection phase.

15. Finally, pressure and flow curves are aligned by synchronization to ECG signals, thus allowing calculation of instantaneous cardiac power. From the power curves, peak power and contractile reserve are obtained.

Also provided are such further peripherals as a data base 22 and a printer 24.

While according to FIG. 4 the image produced by the echo-Doppler device 8 is transferred to computer 16 via VCR 14 and video card 12, an embodiment is envisaged in which the EDD signals producing this image will be directly transferred to computer 16, obviating the need for VCR 14 and video card 12.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for the non-invasive determination of the pressure-volume loop (PVL) of a patient's heart, comprising the steps of:

(a) connecting said patient to an electrocardiograph;

(b) mounting the probe of an echo-Doppler device on the patient in a four-chamber position of the heart enabling it to sense the aortic root and to produce signals representative of the flow waves issuing from said aortic root;

(c) analyzing said signals and obtaining a series of data points as pairs of flow and time, using the QRS complex of the electrocardiogram pattern as a time reference point;

(d) applying a curve-fitting procedure to turn said data points into a flow curve resembling the flow wave issuing from said aortic root;

(e) placing a pressure cuff on the patient's arm and inflating it to a point where all flow in the patient's brachial artery stops;

(f) deflating said cuff at a controlled rate while measuring pressure inside said cuff throughout deflation;

(g) during deflation, sensing blood flow penetrating the barrier constituted by said pressurized cuff, with instantaneous pressure at the aortic root being equal to instantaneous pressure inside said cuff;

(h) obtaining a series of data points from peak systolic to diasystolic pressure, each point consisting of cuff pressure at penetration coupled with the time of its occurrence after the corresponding QRS complex;

(i) applying a curve-fitting procedure to turn said data points into a pressure curve resembling the ascending limb of the aortic pressure wave;

(j) calculating the end systolic pressure (ESP) using the expression

ESP=DP+⅔ (PSP−DP)

where:

DP=diastolic pressure, and

PSP=peak systolic pressure;

(k) calculating volume at point ESP by integrating said flow curve throughout the ejection phase of the patient's heart; and (l) from data obtained in steps (a) through (k), forming said pressure-volume loop;

viewing said pressure-volume loop on a monitor screen.

2. The method as claimed in claim 1, comprising the further step of calculating at least one of the parameters cardiac power, cardiac peak power and contractile reserve, using the expressions:

Cardiac power=flow$_{sys}$×pressure$_{sys}$ where:

$\text{flow}_{sys}$=aortic flow computed from the velocity/time integral×aortic valve area measured in the apical four-chamber view by echo-Doppler, and $\text{pressure}_{sys}$=the central aortic pressure;

Cardiac peak power=$\max(\text{flow}_{sys} \times \text{pressure}_{sys})$ the maximum product of $\text{flow}_{sys}$ and $\text{pressure}_{sys}$, and Contractile reserve=peak $\text{power}_{max}$−peak $\text{power}_{rest}$ the difference between peak power under maximal stress and peak power at rest.

3. The method as claimed in claim 1, comprising the further step of storing all data yielded by said method in a data bank.

4. The method as claimed in claim 1, comprising the further step of producing a print-out of said pressure volume loop as calculated and as imaged on said display means.

5. The method as claimed in claim 1, wherein said signals are produced by an echo-Doppler device and are utilized to generate an image on a CRT screen.

6. The method as claimed in claim 5, comprising the further step of using a VCR to record the image produced by said echo-Doppler device and to transfer said image via a video card to said computer means.

7. A system for the non-invasive determination of the pressure-volume loop of a patient's heart comprising:

electrocardiograph means having electrodes attachable to selected points on the body of said patient;

a pressurizable cuff mountable on an arm of said patient;

computer means provided with display means, connectable to said electrocardiograph means and to said pressurizable cuff via a pressure card, and monitoring means including an echo-Doppler probe located externally of said patient and in position to obtain a four-chamber view of the aortic root of said patient's heart, the output of said means leading, at least indirectly, to said computer means.

8. The system as claimed in claim 7, wherein said pressurizable cuff is provided with at least one sensor responsive to blood flow in the patient's brachial artery penetrating the barrier constituted by said cuff.

9. The system as claimed in claim 8, wherein said monitoring means comprises a display screen.

10. The system as claimed in claim 9, further comprising a VCR adapted to record the image on said display screen and to transfer image signals via a video card to said computer means.

11. The system as claimed in claim 7, further comprising a data base communicating with said computer means.

12. The system as claimed in claim 7, further comprising a printer addressable by said computer means.

* * * * *